United States Patent [19]

Harrington et al.

[11] 4,308,156
[45] Dec. 29, 1981

[54] HYDRAULIC FLUIDS CONTAINING BARON-SILICON COMPOUNDS

[75] Inventors: Colin J. Harrington, Reading; Herbert F. Askew, Pamber Heath, both of England

[73] Assignee: Castrol Limited, Swindon, England

[21] Appl. No.: 184,207

[22] Filed: Sep. 5, 1980

Related U.S. Application Data

[62] Division of Ser. No. 29,856, Apr. 13, 1979, Pat. No. 4,255,586.

[30] Foreign Application Priority Data

Apr. 14, 1978 [GB] United Kingdom ............... 14827/78

[51] Int. Cl.³ .............................................. C09K 5/00
[52] U.S. Cl. .................................. 252/78.3; 252/78.1; 556/402; 556/403
[58] Field of Search ............... 252/783, 78.2; 556/402, 556/403

[56] References Cited

U.S. PATENT DOCUMENTS 2,957,900 10/1910 Groszos ............................... 556/403
3,519,671 7/1970 Markowitz ........................... 556/402

Primary Examiner—Mayer Weinblatt
Attorney, Agent, or Firm—Bacon & Thomas

[57] ABSTRACT

Hydraulic fluids containing novel compounds of the general formula

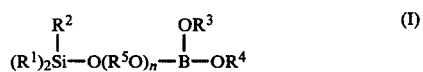

$$(R^1)_2Si-O(R^5O)_n-\overset{\overset{R^2}{|}}{B}-OR^4 \qquad (I)$$

wherein:

(a) each $R^1$ is a hydrocarbyl group, or a group of the formula:

$$-(OR^5)_n-OR^6, \qquad (i)$$

$$-R^5-(OR^5)_n-OR^6, \qquad (ii)$$

$$\underset{\text{or } -OB-O(R^5O)_nR^6}{\overset{O(R^5O)_n-R^6}{|}} \qquad (iii)$$

and each $R^1$ may be the same as, or different from, any other group $R^1$.

(b) $R^2$ is a group as defined for $R^1$, or a group of the formula:

$$-O(R^5O)_nSi(R^1)_3 \qquad (iv)$$

and each group $R^2$ may be the same as, or different from, any other group $R^2$.

(c) each of $R^3$ and $R^4$ is independently a group of the formula:

$$-Si-(R^1)_2 \qquad (v)$$

$$-B-OR^4 \qquad (vi)$$

$$-(R^5O)_n-R^6 \qquad (vii)$$

(d) $R^5$ is an alkylene or an arylene group and each $R^5$ may be the same as, or different from, any other group $R^5$, (e) $R^6$ is a hydrocarbyl group of hydrogens and each group $R^6$ may be the same as, or different from, any other group $R^6$, (f) n is zero or an integer and each n may be the same as, or different from, any other n.

17 Claims, No Drawings

HYDRAULIC FLUIDS CONTAINING BARON-SILICON COMPOUNDS

This is a division of application Ser. No. 29,856, filed Apr. 13, 1979, issued Mar. 10, 1981 and U.S. Pat. No. 4,255,586.

This invention relates to novel chemical compounds which have water scavenging properties, and which are useful as base-stocks or additives for hydraulic fluids.

Their properties make them also useful as water scavenging additives for lubricants, electrical oils and paints.

It is known to use both organosilanes and borate esters as components of hydraulic fluids, for example as disclosed in British Pat. Nos. 1,464,712 and 1,480,738.

Both of these classes of compounds have water scavenging activity. However, borate esters are very hygroscopic and their use as water scavengers for the above-mentioned types of compositions tends to result in the fluid as a whole being undesirably hygroscopic. The organosilanes are much less hygroscopic than borate esters, but have lower scavenging rates.

The novel compounds provided by the invention have the general formula

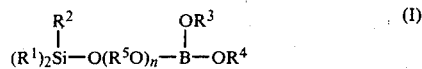
(I)

wherein:

(a) each $R^1$ is a hydrocarbyl group preferably alkyl or aryl, more preferably $C_{1-5}$ alkyl, e.g. methyl or ethyl, or a group of the formula:

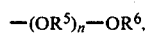 (i)

 (ii)

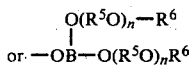 (iii)

and each $R^1$ may be the same as, or different from, any other group $R^1$.

(b) $R^2$ is a group as defined for R, or a group of the formula:

$-O(R^5O)_nSi(R^1)_3$ (iv)

and each group $R^2$ may be the same as, or different from, any other group $R^2$.

(c) each of $R^3$ and $R^4$ is independently a group of the formula:

 (v), (vi), (vii)

(d) $R^5$ is an alkylene or an arylene group preferably ethylene or propylene and each $R^5$ may be the same as, or different from, any other group $R^5$.

(e) $R^6$ is a hydrocarbyl group preferably alkyl, more preferably $C_{1-20}$ alkyl, or hydrogen and each group $R^6$ may be the same as, or different from, any other group $R^6$.

(f) n is zero or an integer preferably no greater than 10, more preferably from 2 to 5, and each n may be the same as, or different from, any other n. Preferably, when any $R^1$ is a group of formula (iii), no group $R^3$ or $R^4$ is a group of the formula (v).

In the present context, hydrocarbyl groups are to be understood to include alkyl, alkenyl, alkynyl, aryl, alkaryl and aralkyl groups.

As stated above each $R^5$ may be the same as or different from any other group $R^5$ and thus it should be appreciated that any group $-(R^5O)_n-$ or $-(OR^5)_n-$ wherein n is an integer greater than 1 may comprise a mixture of different alkyleneoxy and/or aryleneoxy units, preferably a mixture of ethyleneoxy and propyleneoxy units.

A particular characteristic of the compounds of the invention is that they contain a group of the formula $Si-O(R^4O)_n-B$, in which n may be zero or an integer, preferably zero.

One group of preferred compounds according to the invention are those in which $R^3$ and $R^4$ are each the said group of the formula $-(R^5O)_nR^6$, and these compounds may be thought of as substituted silanes. Preferred compounds within this group have the formula:

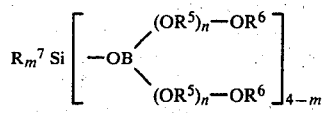

in which m is 1, 2 or 3, and each $R^7$ independently is a hydrocarbyl group or a group of the formula $-(OR^5)_n-OR^6$ and n is from 0 to 5.

Particularly preferred compounds of this kind have the formula $(R^7)_2 Si[OB(OR^9)_2]_2$, in which $R^7$ is as defined above, preferably methyl, and $R^9$ is a $C_6-C_{20}$ alkyl group, or a group of the formula $-(R^5O)_n-Et$ or $-(R^5O)_n-Me$, n is from 2 to 5, and $R^5$ is as defined above.

In a second generally preferred group of compounds according to the invention, each $R^1$ is a hydrocarbyl group or a group of the formula (i) or (ii) as defined above and each $R^2$ is a hydrocarbyl group or a group of the formula (i), (ii) or (iv) as defined above, such compounds may generally be though of as substitute boranes.

A preferred group of compounds in this class have the formula:

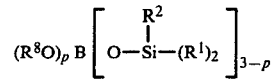

wherein $R^1$ and $R^2$ are as defined immediately above, $R^8$ is a group of the formula $(R^5O)_n-R^6$ and each may be the same as or different from any other, p is 0, 1, or 2, and n is from 0 to 10, preferably 0 to 5.

The compounds of the present invention do not readily lend themselves to conventional nomenclature and for the purpose of naming them an appropriate system has therefore had to be derived. For example, a preferred compound in accordance with the invention which has the formula:

may be called bis bis(methoxyethoxyethoxyethoxy)-boronoxy dimethyl silane but in preference will more simply be called bis bis(methyl triglycol)boronoxy dimethyl silane. Similar preferred compounds include tris bis(methyl triglycol)boronoxy methyl silane and tetra bis(methyl tripropylene glycol)boronoxy silane. Alternatively, as an example of a compound containing one boron atom and more than one silicon atom, the preferred compound having the formula

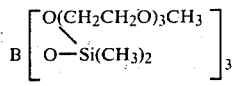

could be called tris(dimethyl methoxyethoxyethoxyethoxysiloxy)borane but in preference will be called tris(methyltriglycol dimethyl siloxy)borane.

The compounds of the present invention have a wide range of uses and may be used for example in situations where silicate esters, siloxanes, silane esters and borate esters have hitherto been used, particularly in applications in which balanced water scavenging preparations are desired. The compounds per se which are generally liquids, may thus be used for example as bases for lubricants, hydraulic fluids and electrical oils.

Alternatively, compounds in accordance with the invention bearing appropriate substituent groups may be soluble in or miscible with for example hydrocarbon oils, silicone oils, natural and synthetic esters e.g. glycerides, aromatic and aliphatic carboxylic acid esters, glycols, glycol ethers and phosphorus esters, acetals and silane derivatives and may thus be employed as components of compositions e.g. lubricants, hydraulic fluids, electrical oils and paints, based upon such materials. For example, compounds in accordance with the invention of the type as hereinbefore specifically mentioned will normally be soluble in and miscible with polyoxalkylene glycols and mono and diethers thereof, enabling the preparation of compositions which are particularly useful as brake fluids for use in hydraulic systems in which the seals are made from natural or styrene butadiene rubbers. In such fluids the amount of the compound of the invention to be included may vary within wide limits but will generally be from 5 to 40% by weight of the composition.

Furthermore, compounds of the type illustrated by the formulae

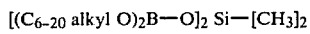

and

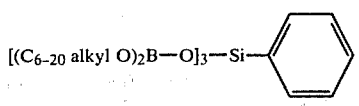

will normally be miscible with hydrocarbon oils and may accordingly be employed in combination therewith in situations where hydrocarbon oils have hitherto been used e.g. in lubricating oils, hydraulic oils, electrical oil, cable and capacitor saturants.

The compounds of the invention may be prepared by reacting the appropriate halosilanes with appropriate boron-containing compounds. The preferred original starting materials for the preparation of the compounds according to the invention are halosilanes (preferably chlorosilanes), and boric acid, as sources of silicon and boron respectively. Whilst the reactions are carried out as if the halogen atoms of halosilanes tend to be decreasingly labile as progressive substitution occurs, there is no evidence to substantiate this fact other than the evidence from elemental analysis and the indirect inferences drawn from spectral analysis. Thus it would appear that the products obtained on substitution of the halogen by, for example, hydroxy compounds, such as alkanols, glycols and glycol ethers can be controlled to a large extent by controlling the stoichiometry of the reactants. The same considerations would appear to apply to the reaction of the hydrogen atoms of boric acid where indeed the literature appears to support the progressive lability of the hydrogen atoms. A preferred process particularly suitable for preparing compounds of the invention which may generally be classed as substituted silanes comprises reacting an appropriate partial borate ester (usually a borate ester having a single B—O—H linkage), which may be prepared for example by heating boric acid and the appropriate hydroxyl compound until the theoretical amount of water has been given off, with an appropriate halosilane, the halogen preferably being chlorine. The number of halogen atoms in the halosilane will generally correspond to the desired number of boron atoms in the product. Thus, in a preferred embodiment, this method comprises reacting $B(OH)_3$ with a compound of formula $HO—(R^5O)_n—R^6$ wherein n, $R^5$ and $R^6$ are each as defined above, and reacting the product with a halosilane of the formula $R^2SiX_2Y$ wherein $R^2$ is as defined above, Y is a halogen atom, and each X independently is a halogen atom or a group of the formula $R^1$ as defined above.

Alternatively for preparing compounds of the invention which may generally be classed as substituted boranes it is preferred to react an appropriate halosilane with an appropriate hydroxyl compound and to react the product with boric acid. The hydroxy-containing compound is usually used in an appropriate stoichiometric amount so as to leave a single chlorine atom bonded to silicon. This reaction may be carried out by known methods, for example by heating the compounds together. The product is then reacted with the appropriate borate ester, which may or may not be previously substituted, according to how many atoms of silicon it is desired to introduce.

The borate esters may be produced by known methods by reaction of boric acid with an appropriate hydroxy-containing compound.

In a preferred embodiment, the method therefore comprises optionally reacting a halosilane of the formula $R^2SiX_2Y$, wherein $R^2$ is as defined above, Y is a halogen atom and each X independently is a halogen atom or a group of the formula $R^1$ as defined above, with a compound of the formula $H(OR^5)_n—OR^6$, and reacting the product with a boric acid compound of the formula $Z_2BOH$ wherein each group Z independently is a hydroxyl group, or a group of the formula $—(OR^5)_n—OR^6$, and $R^5$, $R^6$ and n are each defined above.

Compounds including a B—O—B linkage may be prepared by including a pyroborate or metaborate among the starting materials.

Those of the foregoing reactions involving substitution of halogen on silicon generally evolve hydrogen halide, and this may either be purged, for example with nitrogen, and removed from the system, or the reaction may be carried out in the presence of an appropriate amount of a base, for example ammonia or an amine, such as pyridine which will form a salt with the hydrogen halide. The salt may be separated from the reaction mixture, for example by filtration.

Similarly condensation with boric acids will generally involve the evolution of water, which may be removed by known methods, for example by heating.

It is to be understood that the invention also includes the above-mentioned processes for preparing the compounds of the invention and compositions containing such compounds. Now follow by way of example preparations of typical compounds in accordance with the present invention. In the Examples, parts and percentages are by weight, unless otherwise indicated. The chlorine levels of the compounds prepared in the Examples were generally less than 0.01%.

EXAMPLE 1

Bis[bis (methyltriglycol)boronoxy]dimethyl silane

Boric acid (123.6 g 2 moles), triethyleneglycol monomethylether (methyl triglycol) (656 g, 4 moles) and toluene (2.5 liters) were heated with stirring in a glass vessel under a Dean & Stark apparatus until 72 ml (4 moles theoretical) of water were removed. The mixture was cooled and pyridine (158 g 2 moles) added followed by the dropwise addition of dimethyldichlorosilane (129 g 1 mole) at about 40° C. After the moderate exotherm had subsided the mixture was heated for 2 hours at 70° C., filtered and stripped on a rotary evaporator at 120°/40 mmHg followed by stripping under high vacuum to a base temperature of 150° C. at 0.1 mmHg. After filtration through a filter aid the product (722 g 94.5%) was a clear yellow liquid containing 2.76% boron, 3.27% silicon and 0.11% chlorine.

This analysis corresponds well with the compound in the heading above, the theoretical values being 2.88% boron and 3.66% Silicon. These theoretical values would also correspond to a mixture of the compound [CH$_3$(OCH$_2$CH$_2$)$_3$O]$_2$Si(CH$_3$)$_2$ and methyl triglycol metaborate. However the metaborate has a characteristic peak in the infrared at 720 cm$^{-1}$ which was absent in the compound isolated.

The product had a viscosity at $-40°$ C. of 3321 cSt and when tested for rubber swell properties in accordance with the SAE J1703 specification gave the following results:
SBR G9: 8.8%
Natural R32: 1.5%

EXAMPLE 2

Tris(bis(methyltriglycol) boronoxy)methylsilane

This product was prepared substantially as in Example 1 but using the following reactants:
Boric acid (185.4 g, 3.0 mole)
Triethylene glycol monomethyl ether (984.0 g, 6.0 mole)
Pyridine (237.0 g, 3.0 mole)
Trichloromethylsilane (149.5 g, 1.0 mole)

The product (1006 g, 91.3%) was a yellow liquid containing 2.67% silicon (theoretical 2.54%) and 2.78% boron (theoretical 2.94%).

EXAMPLE 3

Tris(methyl triglycol dimethylsiloxy)borane

A mixture of pyridine (260.7 g, 3.3 mole) and triethyleneglycol monomethylether (492.0 g, 3.0 mole) was added to a mixture of dimethyl dichlorosilane (387.0 g, 3.0 mole) and toluene (1.0 liters) with cooling. The total mixture was then heated at 100° C., for 1½ hours. When the mixture had cooled, and after filtration, boric acid (68.0 g, 1.1 mole) and pyridine (260.7 g, 3.3 mole) were then added alternately portionwise with the production of a mild exotherm. The reaction was completed by heating for 4 hours at 100° C. after which time the solid was removed by filtration. The solvent was stripped off using a rotary evaporator and any volatiles by stripping to 185° C. at 0.4 mmHg. The product was finally filtered to give 460 g (63.6%) of a yellow liquid containing 1.85% boron (theoretical 1.52%) and 11.6% silicon (theoretical 11.62%).

In each of Examples 4 to 38 the amount of pyridine used was such as to be equimolar with the theoretical amount of HCl produced, or in slight excess.

EXAMPLES 4 to 22

Preparations were carried out in the same manner as described in Example 1, but using the hydroxy-containing compounds shown in Table 1, in place of the triethyleneglycol monomethylether in approximately the same molar proportions, to produce compounds of the general formula:

Me$_2$Si[OB(OR)$_2$]$_2$

R being the residue of the hydroxy-containing compound.

The theoretical and experimentally determined silicon and boron contents are also shown in Table 1.

TABLE 1

| Example No: | Alcohol (ROH) used | % Silicon (theoretical value) | % Boron (theoretical value) |
|---|---|---|---|
| 4 | Ethylene glycol monobutylether | 4.61 (4.83) | 3.44 (3.72) |
| 5 | Diethylene glycol monomethylether | 4.58 (4.76) | 3.46 (3.67) |
| 6 | Triethylene glycol monomethylether | 3.88 (3.66) | 2.72 (2.83) |
| 7 | Diethylene glycol monoethylether | 4.17 (4.35) | 3.33 (3.35) |
| 8 | Triethylene glycol monoethylether | 3.37 (3.41) | 2.48 (2.63) |
| 9 | Dipropylene glycol monomethylether | 4.13 (4.00) | 3.01 (3.09) |
| 10 | Triethylene glycol monomethylether | 3.03 (3.00) | 2.35 (2.32) |
| 11 | (1) | 2.40 (2.60) | 1.93 (2.01) |
| 12 | (2) | 2.77 (3.26) | 2.49 (2.51) |
| 13 | (3) | 2.75 (3.20) | 2.35 (2.47) |
| 14 | (4) | 3.05 (3.00) | 2.04 (2.32) |
| 15 | (5) | 1.82 (2.21) | 1.70 (1.70) |
| 16 | n-hexanol | 5.23 (5.43) | 3.82 (4.19) |
| 17 | 2-ethylhexanol | 4.36 (4.46) | 2.82 (3.44) |
| 18 | branched tridecanol | 2.86 (3.08) | 2.04 (2.38) |
| 19 | 2-methylcyclohexanol | 5.08 (4.96) | 3.63 (3.83) |
| 20 | o-cresol | 5.12 (5.20) | 4.01 (4.00) |
| 21 | 2-phenoxyethanol | 3.66 (4.24) | 2.91 (3.27) |
| 22(6) | Triethylene glycol monomethylether | 3.86 (3.67) | 2.78 (2.83) |

(1) was a commercially available ethylene/propylene glycol ether supplied by Dow Chemical Company (E555) having an equivalent weight of about 243 and wherein the terminal ether alkyl groups are believed to be predominantly methyl but with a proportion being ethyl. Its boiling point is 290° C.

(2) was a commercially available mixture of polyoxyethylene glycol monomethyl ethers having an equivalent weight of about 188 and a boiling point of about 260° C.

(3) was a commercially available ethylene/propyleneglycol monoethyl ether having a boiling point of 260° C. and an equivalent weight of 192.

(4) was a commercially available mixture of polyoxyethylene glycol ethyl and butyl ethers, having an equivalent weight of 207.

(5) was a commercially available mixture of $C_{12}$ and $C_{14}$ alcohols wih an average of three oxyethylene groups attached.

(6) in this preparation the solvent used was carbon tetrachloride.

EXAMPLES 23 and 24

Compounds of the general formula $Et_2Si[OB(O[CH_2CH_2O]_3Me)_2]_2$ and (23)

$C_6H_5MeSi[OB(O[CH_2CH_2O]_3Me)_2]_2$ (24)

were prepared in the same manner as in Example 1, but using diethyldichlorosilane, and methylphenyldichlorosilane respectively, in place of dimethyldichlorosilane. The theoretical and measured silicon and boron content are shown below in the same manner as in Table 1.

|  | % Si | % B |
|---|---|---|
| Example 23 | 3.54 (3.54) | 2.61 (2.72) |
| Example 24 | 2.99 (3.39) | 2.59 (2.62) |

EXAMPLES 25 to 28

The procedure was the same as in Example 2, except that the hydroxy-compounds shown in Table 2 were used in place of trimethyleneglycol monomethylether in approximately stoichiometric proportions, to produce compounds of the general formula $MeSi[OB(OR)_2]_3$, R being the residue of the hydroxy-containing compound.

TABLE 2

| | | Analysis | |
|---|---|---|---|
| Example No: | Alcohol (ROH) used | % Silicon (theoretical value) | % Boron (theoretical value) |
| 25 | Diethylene glycol monomethylether | 3.61 (3.34) | 3.39 (3.87) |
| 26 | n-hexanol | 3.71 (3.84) | 3.66 (4.44) |
| 27 | Tripropylene glycol monomethylether | 2.13 (2.07) | 1.93 (2.40) |
| 28 | Tripropylene glycol monomethylether | 2.22 | 2.24 |

In Example 28, the conditions and reagents were the same as in Example 27. As can be seen from Table 2, the silicon and boron content of the products were slightly different.

EXAMPLE 29

Preparation of $C_5H_{11}Me_2Si\,OB(O[CH_2CH_2O]_3Me)_2$
The procedure was the same as in Example 1, except that pentyldimethylchlorosilane was used in place of dimethyldichlorosilane. The product was analysed and determined to have a silicon content of 6.11% (theoretical 5.81%) and a boron content of 1.88% (theoretical 2.24%).

EXAMPLE 30

Preparation of

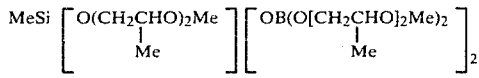

The procedure was the same as in Example 1, except dipropyleneglycol monomethylether was used instead of triethyleneglycol monomethylether in an approximately stoichiometric amount, and

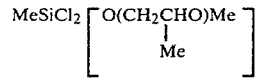

instead of dimethyldichlorosilane. The silicon content of the product was found to be 3.37% (theoretical 3.37%) and the boron content 2.57% (theoretical 2.60%).

EXAMPLE 31

Preparation of $MeSi[O(CH_2CH_2O)_2Me]_2[OB(O[CH_2CH_2O]_2Me)_2]$

The procedure was the same as in Example 1, except that diethyleneglycol monomethylether was used in place of triethyleneglcyol monomethylether in approximately the appropriate stoichiometric amount, and $MeSiCl\,[O(CH_2CH_2O)_2Me]_2$ was used in place of $Me_2Si\,Cl_2$. The silicon content of the product was found to be 35% (theoretical 5.13%) and the boron content 2.14% (theoretical 1.98%).

EXAMPLES 32 to 35

Preparation of compounds of the formula $Me_2Si[OR'][OB(OR'')_2]$

The procedure was the same as in Example 1, except that the appropriate alcohol R"OH (4 moles) was used in place of dimethyleneglycol monomethylether in approximately the appropriate stoichiometric amounts, and $Me_2Si(OR')\,Cl$ was used in place of $Me_2Si\,Cl_2$. The results are shown in Table 3.

TABLE 3

| | | Analysis | |
|---|---|---|---|
| Example No: | Alcohol Residue | % Silicon (theoretical value) | % Boron (theoretical value) |
| 32 | R' = —(CH$_2$CH$_2$O)$_3$Me<br>R" = —(CH$_2$CH$_2$O)$_3$Me | 4.93 (4.88) | 1.97 (1.88) |
| 33 | R' = —(CH$_2$CH$_2$O)$_2$Et<br>R" = —(CH$_2$CH$_2$O)$_2$Et | 5.49 (5.79) | 2.42 (2.23) |
| 34 | R' =<br>R" = —CH$_2$CH(CH$_2$)$_3$Me<br>　　　　　｜<br>　　　　　Et | 5.12 (5.93) | 2.36 (2.29) |
| 35 | R' = —CH$_2$CH$_2$O H<br>R" = —(CH$_2$CH$_2$O)$_3$Et | 8.11 (6.79) | 3.06 (2.62) |

EXAMPLE 36

The procedure was the same as used in Example 3, except that the material referred to in footnote 1 to Table 1 was used in place of triethyleneglycol monomethylether, to produce a compound of the general formula:

$$B[OSi(OR^8)Me_2]_3$$

wherein $R^8$ is the residue of the said ethylene/propylene glycol ether. The silicon and boron contents of the product were 7.94 and 1.13 (calculated 8.79 and 1.13) respectively.

EXAMPLE 37

Preparation of $(RO)B[OSi(OR)Me_2]_2$ $(R=(CH_2CH_2O)_2Et)$

The procedure was the same as in Example 3, except that diethyleneglycol monoethylether was used in place of triethyleneglycol monomethylether in an approximately stoichiometric amount, and $(RO)B(OH)_2$ in place of boric acid. The silicon content of the product was found to be 11.3% (theoretical 10.04%) and the boron content 1.37% (theoretical 1.94%).

EXAMPLE 38

Preparation of $(RO)B$ $OSi(OR)_2Me_2$ $(R=(CH_2CH_2O)_2Et)$

The procedure was the same as in Example 37, except that methyltrichlorosilane was used in place of dimethyldichlorosilane, in an approximately stoichiometric amount. The silicon content of the product was found to be 7.98% (theoretical 7.05%) and the boron content 1.50% (theoretical 1.36%)

EXAMPLES 39 to 80

Formulation of hydraulic fluids.

In order to assess the suitability of the compounds prepared in Examples 2 to 38 as components of hydraulic fluids two types of blends were prepared. The first type consisted of 30% by weight of the compound indicated and 0.2% cyclohexylamine, the balance being triethyleneglycol monomethylether. The blends are shown in Table 4.

The second type of blend consisted of 10% by weight of the compound indicated and 5% Primene JMT (Trade Mark) the balance being a gas oil to the DTD585B specification having a viscosity at 100° C. of 1.2 cSt. The blends are shown in Table 5.

In each case the viscosity at −40° C. was determined and in the vast majority of cases found to be well within the requirements of the various specifications laid down for automotive hydraulic fluids.

Rubber swell properties were evaluated for styrene/butadiene (SBR) (G9) natural (R32), and nitrile rubbers (A79). These were determined by measuring the percentage increase in volume of a 1 inch (2.54 cm) square 2 mm thick rubber specimen in 50 mls of test fluid. The duration of the test in each case was three days, and the temperature was 120° C. for SBR and 70° C. for the natural and nitrile rubbers.

Vapour lock temperatures were determined before (dry) and after subjecting the fluid to a Humidity Test essentially according to the FMVSS 116 Specification.

The vapour lock was determined on the Castrol Vapour Lock Indicator. In this device a small fixed size sample of fluid is heated at a standard rate in an enclosed container (boiler) having a small outlet.

The detailed description of the Castrol Vapour Lock Indicator is given in U.S. Pat. No. 3,844,159.

When the vapour lock temperature is reached, the sudden formation of vapour in the boiler ejects fluid through the small outlet into a container, where its presence is detected. The temperature of the fluid in the boiler when this occurs is measured and is defined as the vapour lock temperature.

TABLE 4

| Example No: | Example No. of Compound of Invention | Viscosity (cSt) at −40° C. | Rubber Swell (3 day test) | | Vapour Lock Temp (°C.) | |
|---|---|---|---|---|---|---|
| | | | SBR | Natural | Dry | after D.O.T. Humidity |
| 39 | 4 | 475 | 19.1 | 7.5 | 206 | 153 |
| 40 | 5 | 417 | 6.4 | −0.3 | 211 | 165 |
| 41 | 6 | 557 | 6.0 | −1.5 | 229 | 160 |
| 42 | 7 | 443 | 9.7 | 0.85 | 215 | 163 |
| 43 | 8 | 582 | 6.9 | 0.2 | 226 | 158 |
| 44 | 9 | 489 | 13.2 | 2.9 | 213 | 158 |
| 45 | 10 | 569 | 12.0 | 2.5 | 225 | 159 |
| 46 | 11 | 692 | −1.1 | 0.1 | 230 | 157 |
| 47 | 12 | 678 | 4.8 | −0.07 | 233 | 159 |
| 48 | 13 | 629 | 6.8 | 0.5 | 232 | 161 |
| 49 | 14 | 498 | 6.4 | 0.6 | 231 | 156 |
| 50 | 15 | solid | 19.5 | 8.5 | 229 | 152 |
| 51 | 20 | 10535 | 10.7 | 1.7 | 222 | 162 |
| 52 | 21 | 4452 | 9.9 | 1.2 | 232 | 157 |
| 53 | 22 | 647 | 6.5 | −0.33 | — | — |
| 54 | 23 | 512 | 6.3 | — | 238 | (169) |
| 55 | 24 | 1350 | 6.6 | 0.05 | 227 | 157 |
| 56 | 2 | 671 | — | −0.5 | — | 160 |
| 57 | 25 | 482 | 6.1 | 0.1 | 215 | 160 |
| 58 | 27 | 553 | 12.2 | 18.2 | 221 | 149 |
| 59 | 28 | 961 | 13.5 | 3.1 | 229 | 160 |
| 60 | 29 | 792 | 19.3 | — | — | — |
| 61 | 30 | 493 | 9.4 | 2.1 | 220 | 161 |
| 62 | 31 | 380 | 7.3 | 0.7 | 228 | 160 |
| 63 | 32 | 458 | 5.4 | 0.5 | 237 | 162 |
| 64 | 33 | 345 | 10.0 | 2.5 | 230 | 161 |
| 65 | 35 | 738 | 9.9 | 2.1 | 235 | 163 |
| 66 | 3 | 429 | 7.7 | 0.4 | 246 | 163 |
| 67 | 36 | 514 | 6.6 | −2.2 | 240 | 163 |
| 68 | 37 | 401 | 11.0 | 3.3 | 231 | 155 |
| 69 | 38 | 401 | 9.3 | 1.4 | 163 | 159 |

TABLE 5

| Example No: | Example No. of Compound of Invention | Viscosity (cSt) at −40° C. | Rubber Swell (3 day test) on A79 nitrile rubber | Vapour Lock Temp (°C.) | |
|---|---|---|---|---|---|
| | | | | Dry | 0.2% Water |
| 70 | 7 | 186 | 10.8 | 245 | 221 |
| 71 | 9 | 189 | 8.8 | 245 | 229 |
| 72 | 10 | 197 | 6.9 | 248 | 231 |
| 73 | 16 | 158 | 3.5 | 242 | 189 |
| 74 | 17 | 153 | 4.4 | 245 | — |
| 75 | 18 | 259 | 5.1 | 240 | 200 |
| 76 | 19 | 255 | 4.6 | 245 | 211 |
| 77 | 26 | 131 | 2.0 | 241 | 189 |
| 78 | 27 | 194 | 7.4 | 241 | 209 |
| 79 | 30 | 186 | 7.5 | 241 | 209 |
| 80 | 34 | 178 | 3.4 | 240 | 180 |

As is evidenced by the foregoing Examples 39 to 80, the use of the compounds of the invention in hydraulic fluids in amounts as low as 10% can provide fluids which are not excessively hygroscopic, and yet in which the compounds of the invention provide a sufficiently high scavenging rate, as evidenced by the retention of high vapour lock temperatures throughout the life of the fluid.

When the compounds are used in other fluids such as electrical oils, much smaller amounts can be used.

EXAMPLE 81

Preparation of $B(OCH_2CH_2OSiMe_3)_3$ a mixture of ethylene glycol (409.2 g, 6.6 mole) and boric acid (136 g, 2.2 mole) was heated using carbon tetrachloride as azeotroping agent and 118.8 ml of water were removed. To this mixture was added pyridine (521.4 g, 616 mole) followed by Trimethyl chlorosilane (651 g, 6 mole). The mixture was heated at 80° C. for 4 hours then filtered and stripped of volatiles to 120° C. at 20 mmHg and filtered.

Analysis showed the product to contain 3.44% boron and 18.2% silicon (calculated 2.64% and 20.5% respectively).

We claim:

1. A hydraulic fluid composition consisting essentially of at least about 5% by weight based on the weight of the composition of a compound of the general formula:

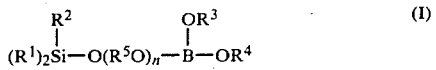

wherein:

(a) each $R^1$ is a hydrocarbyl group, or a group of the formula:

 (i)

 (ii)

 (iii)

and each $R^1$ may be the same as, or different from, any other group $R^1$, (b) $R^2$ is a hydrocarbyl group or a group of the formula (i), (ii), or (iii) as defined above, or a group of the formula:

 (iv)

and each group $R^2$ may be the same as, or different from, any other group $R^2$, (c) each of $R^3$ and $R^4$ is independently a group of the formula:

 (v)

 (vi)

 (vii)

(d) $R^5$ is an alkylene or an arylene group and each $R^5$ may be the same as, or different from, any other group $R^5$, (e) $R^6$ is a hydrocarbyl group or hydrogen and each group $R^6$ may be the same as, or different from, any other group $R^6$, (f) n is zero or an integer and each n may be the same as, or different from, any other n, (g) each $R^{11}$ and $R^{12}$ independently is a hydrocarbyl group or a group of the formula (i) or (ii) as defined above, and $R^{10}$ is an aryl group or a group of the formula (i), (ii) or (iv) as defined above, (h) provided that when $R^1$ or $R^2$ is a group of formula (iii), $R^3$ and $R^4$ are each not a group of formula (v); together with one or more conventional hydraulic fluid components selected from the group consisting of hydrocarbon oils, silicone oils, natural and synthetic esters, glycols, glycol ethers, phosphorus esters, acetals and silane derivatives.

2. A hydraulic fluid composition as claimed in claim 1, containing a compound of the formula (I) wherein $R^2$, or each $R^2$, is a phenyl group, the residue of a glycol ether, an alkoxy group, or a group of the formula: $-OB[O(R^5O)_n-R^6]_2$.

3. A hydraulic fluid composition as claimed in claim 1, containing a compound of the formula (I) wherein $R^5$ is ethylene or propylene.

4. A hydraulic fluid composition as claimed in claim 1, containing a compound of the formula (I) wherein n or each n is zero or an integer from 1 to 5.

5. A hydraulic fluid composition as claimed in claim 1 which contains from about 5 to 40% by weight of said compound of formula (I).

6. A hydraulic fluid as claimed in claim 1, wherein $R^3$ and $R^4$ are each independently a group of the formula:

 (vii)

7. A hydraulic fluid composition as claimed in claim 6, wherein the compound has the general formula:

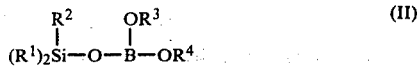 (II)

8. A hydraulic fluid composition as defined in claim 1, wherein in the compound of the general formula (I) each $R^1$ independently is a hydrocarbyl group, or a group of the formula (i) or (ii) as defined in claim 30, and $R^2$ is an aryl group or a group of the formula (i), (ii) or (iv) as defined in claim 1.

9. A hydraulic fluid composition as claimed in claim 8 wherein the compound has the general formula:

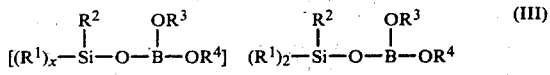 (III)

10. A hydraulic fluid composition as claimed in claim 1, containing a compound of the formula (I) wherein $R^1$, or each $R^1$, is an alkyl group, a phenyl group, the residue of a glycol ether or an alkoxy group.

11. A hydraulic fluid composition as claimed in claim 10, wherein $R^1$, or each $R^1$, of the defined compound is a methyl group.

12. A hydraulic fluid composition as claimed in claim 1, containing a compound of the formula (I) wherein $R^6$, or each $R^6$, is a $C_1$-$C_{20}$ alkyl group.

13. A hydraulic fluid composition as claimed in claim 12, wherein $R^6$, or each $R^6$ of the defined compound is methyl or ethyl.

14. A hydraulic fluid composition consisting essentially of at least about 5% by weight based on the weight of the composition of a compound of the general formula:

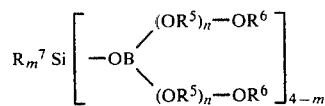

wherein each $R^7$ independently is a hydrocarbyl group, or a group of the formula:

$$-(OR^5)_n-OR^6\text{ ps}$$

n is 0 or an integer from 1 to 5, m is 1, 2, or 3, $R^5$ is an alkylene or an arylene group and each $R^5$ may be the same as, or different from, any other group $R^5$, and $R^6$ is a hydrocarbyl group or hydrogen and each group $R^6$ may be the same as, or different from, any other group $R^6$; together with one or more conventional hydraulic fluid components selected from the group consisting of hydrocarbon oils, silicone oils, natural and synthetic esters, glycols, glycol ethers, phosphorus esters, acetals and silane derivatives.

15. A hydraulic fluid composition consisting essentially of at least about 5% by weight based on the weight of the composition of a compound of the general formula:

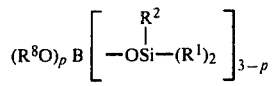

wherein each $R^1$ independently is a hydrocarbyl group or a group of the formula:

$$-(OR^5)_n-OR^6 \quad \text{(i)}$$

or $$-R^5-(OR^5)_n-OR^6 \quad \text{(ii)},$$

each $R^2$ independently is an aryl group or a group of the formula:

$$-(OR^5)_n-R^6 \quad \text{(i)}$$

or $$-R^5-(OR^5)_n-R^6 \quad \text{(ii)}$$

or $$-O(R^5O)_nSi(R^{12})_3 \quad \text{(iv)}$$

wherein each $R^{12}$ independently is a hydrocarbyl group or a group of the formula (i) or (ii) as defined above, $R^8$ is a group of the formula:

$$-(R^5O)_n-R^6$$

and each group $R^8$ may be the same as, or different from any other group $R^8$, p is 0, 1 or 2, and $R^5$ is an alkylene or an arylene group and each $R^5$ may be the same as, or diferent from, any other group $R^5$, $R^6$ is a hydrocarbyl group or hydrogen and each group $R^6$ may be the same as, or different from, any other group $R^6$ and n is 0 or an integer from 1 to 5; together with one or more conventional hydraulic fluid components selected from the group consisting of hydrocarbon oils, silicone oils, natural and synthetic esters, glycols, glycol ethers, phosphorus esters, acetals and silane derivatives.

16. A hydraulic fluid composition consisting essentially of at least about 5% by weight based on the weight of the composition of a compound of the general formula:

$$Me_2Si[OB(OR^9)_2]_2$$

wherein $R^9$ is a $C_6$ to $C_{20}$ alkyl group or a group of the formula $-(R^5O)_n-Et$ or $-(R^5O)_n-Me$, wherein n is from 2 to 5, and $R^5$ is an alkylene or an arylene group and each $R^5$ may be the same as, or different from, any other group $R^5$; together with one or more conventional hydraulic fluid components selected from the group consisting of hydrocarbon oils, silicone oils, natural and synthetic esters, glycols, glycol ethers, phosphorus esters, acetals and silane derivatives.

17. A hydraulic fluid composition as claimed in claim 16, containing a compound of the recited formula wherein $R^9$ is $-(CH_2CH_2O)_3Me$.

* * * * *